| United States Patent [19] | [11] | 4,243,827 |
|---|---|---|
| Ryu | [45] | Jan. 6, 1981 |

[54] PROCESS FOR THE CONVERSION OF AROMATIC HYDROCARBONS

[75] Inventor: Ji-Yong Ryu, Des Plaines, Ill.

[73] Assignee: UOP Inc., Des Plaines, Ill.

[21] Appl. No.: 28,015

[22] Filed: Apr. 6, 1979

[51] Int. Cl.$^3$ .............................................. C07C 2/70
[52] U.S. Cl. ............................... 585/463; 252/429 A; 585/470; 585/477
[58] Field of Search ................ 585/462, 470, 477, 463

[56] References Cited

U.S. PATENT DOCUMENTS

| 4,048,247 | 9/1977 | Ryu | 585/462 |
|---|---|---|---|
| 4,048,248 | 9/1977 | Ryu | 585/462 |
| 4,061,689 | 12/1977 | Ryu et al. | 585/462 |
| 4,069,268 | 1/1978 | Siskin et al. | 585/462 |

Primary Examiner—C. Davis
Attorney, Agent, or Firm—James R. Hoatson, Jr.; John G. Cutts, Jr.; William H. Page, II

[57] ABSTRACT

A process for the conversion of aromatic hydrocarbons, e.g., reacting an alkylating agent, preferably an olefin, with an aromatic hydrocarbon. The process uses a novel catalyst prepared by subjecting alumina to an anhydrous tetravalent titanium flouride complex of an organic compound selected from the group of organic compounds containing at least one methoxy group per molecule or organic compounds having at least one electron donor atom and double bond per molecule, and heat treating the resulting impregnated alumina in an inert atmosphere.

16 Claims, 2 Drawing Figures

Figure 1:
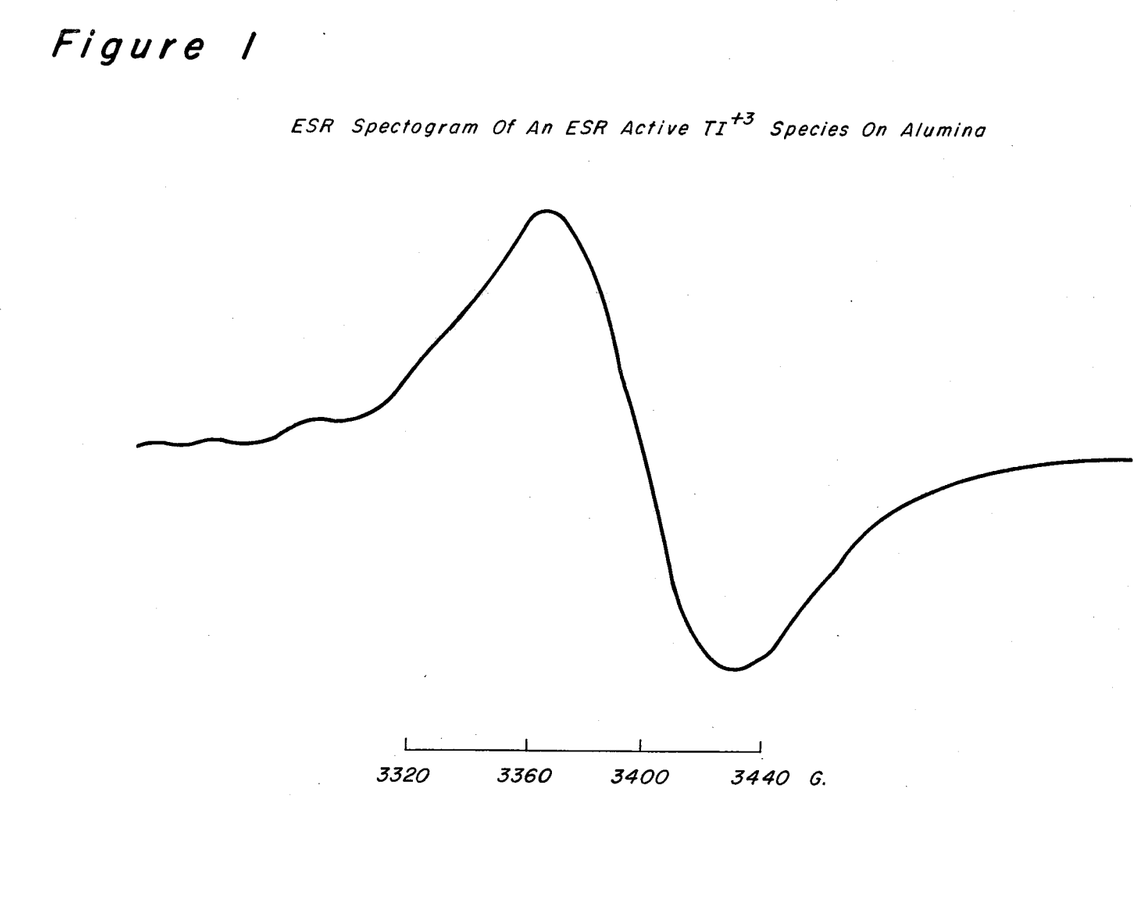

Figure 1  ESR Spectogram Of An ESR Active $Ti^{+3}$ Species On Alumina

Figure 2

Correlation Of Peak Heights Of A $TI^{+3}$ ESR Signal And The Transalkylation Of Ethylbenzene

PROCESS FOR THE CONVERSION OF AROMATIC HYDROCARBONS

BACKGROUND OF THE INVENTION

1. Field of the Invention

The present invention relates to an improved process for the conversion of an aromatic hydrocarbon in the presence of a low valent titanium compound on an inorganic oxide catalyst.

The invention is described with reference to the alkylation of benzene with ethylene, transalkylation of ethylbenzene and methyl group containing aromatic compounds in the presence of the catalyst. The invention can also be used in alkylation and isomerization of alkyl-aromatic compounds.

2. Description of the Prior Art

Conversion of aromatic hydrocarbons is well known in industry. Some of the aromatic conversion reactions which occur include alkylation of aromatic hydrocarbons with an alkylating agent such as an olefin, disproportionation or transalkylation of alkyl aromatics and isomerization of alkyl aromatic such as xylenes, and of dialkyl and higher substituted aromatics.

Of special interest, has been the alkylation of benzene to ethylbenzene, or cumene. Ethylbenzene may be dehydrogenated to make styrene, while cumene is used for the production of phenol and acetone. Cumene is also dehydrogenated to form methylstyrene, in a process similar to that used to convert ethylbenzene to styrene. Ethylbenzene and cumene may also be used as blending components in aviation gasoline because of their high octane number.

It is well known that cumene can be synthesized from benzene and propylene using a catalyst of $AlCl_3$, SPA, or $BF_3$. SPA is a generally accepted abbreviation for solid phosphoric acid catalyst, or phosphoric acid which is absorbed on kieselguhr or other support.

Ethylbenzene can be synthesized from benzene and ethylene using $AlCl_3$ in the presence of catalyst activating agents or co-catalysts such as HCl or alkyl chlorides but SPA is not used commerically for this purpose. $AlCl_3$ is a very popular alkylation catalyst, because of its high activity and good yield. Unfortunately, the catalyst operates as a slurry or sludge which is unruly to handle on a commerical scale, and also is corrosive. A current improved process employs reduced amounts of $AlCl_3$ at higher reaction temperatures. The highly reactive nature of this Friedel-Crafts metal halide catalyst, $AlCl_3$, is desirable when attempting to alkylate benzene with ethylene, because less active catalyst systems do not work.

Another process employs a high silica/alumina ratio zeolite catalyst utilized in a fixed bed process. Since the catalyst activity is weak compared to Friedel-Crafts metal halide catalysts and the reaction is necessarily performed in vapor phase, the reaction temperature is quite high and in the range of 650°-900° F. In this process, the benzene to ethylene ratio is relatively high to minimize frequent catalyst regenerations. The yeild of alkylated products is less than expected from Friedel-Crafts metal halide catalyst process, even at high benzene to ethylene ratios which requires more frequent catalyst regenerations.

Another highly selective catalyst system has been developed for the alkylation of benzene with olefins. This catalyst comprises boron trifluoride. The trifluoride catalyst system is exceptionally active and permits operation with dilute olefin streams, but it requires the continuous addition of $BF_3$ to maintain catalyst activity. High catalyst activity also leads to oligomerization of olefins so that the contact time of olefins with $BF_3$ catalyst should be as short as possible. This catalyst is also exceptionally water sensitive, as water not only destroys the catalyst, but produces very corrosive solutions which attack downstream processing units. $BF_3$ also frequently appears in the product, and must be removed therefrom.

Because of the interest in alkylation of benzene with ethylene and transalkylation of ethylbenzene with olefins, and because of the inadequacies of existing catalyst systems, I studied the work that others had done, and made exhaustive investigations to determine if it would be possible to find a catalyst which would have the activity and selectivity required to produce an acceptable product, while making maximum use of existing petroleum resources.

A highly active catalyst was sought, to permit operation, at attractive temperatures with less utility cost, cost of construction, and to operate with less catalyst. In new units this would mean smaller, and cheaper reactor vessels, while in existing units it would means that an increase in capacity could be obtained by changing catalyst in an existing reactor vessel with minor modifications.

There has been extensive work done with Ti catalysts, though most work occurred in conjunction with studies of Ziegler Natta catalysts. The closest prior art known is U.S. Pat. No. 2,381,481 (Class 260-638.15), U.S. Pat. No. 2,951,885 (Class 260-671), U.S. Pat. No. 2,965,686 (Class 260-671) and U.S. Pat. No. 3,153,634 (Class 252-429).

In U.S. Pat. No. 2,381,481, preparation and use of a catalyst prepared by treating alumina gel with fluorotitanic acid is disclosed. This catalyst is used for polymerization of olefins to heavier hydrocarbons, and also for alkylation of paraffins with olefins, the latter when operating at high temperatures, between 700° and 900° F. or higher. No mention is made of alkylation of aromatics with olefinic hydrocarbons or transalkylation of polyalkybenzenes.

In U.S. Pat. No. 2,951,885, there is disclosed the use of titanium trihalide on activated alumina or other activated acidic oxide for alkylation of benzene with olefins. The catalyst is originally a tetrachloride, subsequently reduced to the trichloride with an alkali metal such as sodium, lithium, or potassium. The examples show that this catalyst will alkylate benzene with ethylene.

In U.S. Pat. No. 2,965,686, the thrust of the application was to develop a titanium subchloride catalyst. The subchloride catalyst was prepared by reacting titanium metal, in the form of turnings, with titanium tetrachloride. The patentee speculated, but gave no examples, showing that it would be possible to form the subchloride by reduction of titanium tetrachloride with hydrogen.

In U.S. Pat. No. 3,153,634, there is disclosed the use of titanium subhalides in a polymerization reaction. The patentee is probably describing catalyst to make solid polymer, as he discussed production of solid polymer products. The patentee seems to teach that the halides all act equivalently. The patentee in U.S. Pat. No. 3,153,634 taught the very antithesis of applicant's process, on page 3 line 65-75 where he mentions use of benzene as an inert solvent to hold dissolved olefins, rather than as a reactant.

SUMMARY OF THE INVENTION

Accordingly, the present invention provides a process for the catalytic conversion of an aromatic hydrocarbon comprising contacting the aromatic hydrocarbon with a reactant in the presence of a catalyst prepared by impregnating active alumina with complexes of $TiF_{4-x}Cl_x$, wherein x equals zero or one, in organic solvents and subjecting the titanium complex compounds supported on alumina at elevated temperatures in an inert gas flow to reduce tetravalent titanium ions to specific trivalent titanium ions in the catalyst, and recovering a converted aromatic hydrocarbon as a product of the process.

The complexes of $TiF_{4-x}Cl_x$ are prepared by reacting $TiF_{4-x}Cl_x$ with organic compounds having at least one methoxy group per molecule selected from the group of organic compounds or organic compounds having at least one electron donor atom and double bond per molecule. If the organic compounds are liquids and the complex compounds are soluble in these organic compounds, the organic compounds can serve as complexing agents and also solvents to prepare the solutions which can be used for the impregnation of alumina.

DETAILED DESCRIPTION

The catalyst of the present invention comprises a low valent titanium compound on a suitable support containing inorganic oxides preferably alumina.

Specific examples of the inorganic metal oxides include alumina, gallium oxide, indium oxide, the thallium oxide. Of these compounds, the preferred support is alumina, and especially low density, high surface areas aluminas such as gamma-alumina or, if so desired, eta-alumina.

The apparent bulk density of the alumina is preferably 0.3 to 0.8 $g/cm^3$, with a surface area of 1 to 500 $m^2/g$. The alumina may be in any shape, e.g., spheroidal alumina, as prepared by the well known oildrop method. The alumina may be treated to provide greater physical stability, e.g., impregnated with a compound such as barium nitrate, which upon calcination is converted into barium oxide.

A commerical gamma-alumina may also be used as the support. Since this commerical gamma-alumina could contain an excessive amount of water which would consume an excess of titanium tetrahalide without any beneficial effect on the catalyst, in the preferred embodiment of this invention, the commerical gamma-alumina is subjected to a predrying step by heating to 250° to 650° C. in inert gas or hydrogen flow for 1 to 10 hours.

Anhydrous $TiF_{4-x}Cl_x$, wherein x equals zero to three, compounds are known to form various octahedral Ti (IV) complexes with neutral organic compounds which have electron donor atoms or groups such as alcohols, ethers, ketones, etc. Anhydrous $TiCl_4$, can also form complexes. However, many $TiCl_4$ complex samples formed with alcohol or ether, produced various titanium chloralkoxides by alcoholysis which are insoluble in organic solvents or a heated mixture of $TiO_2$ and titanium oxychloride. Therefore, $TiCl_4$ or $TiCl_4$ complexes are not suitable for the preparation of a suitable catalyst. There has been no previous evidence that the complexes of $TiF_{4-x}Cl_x$, wherein x equals zero or one formed by the reaction of $TiF_{4-x}Cl_x$, wherein x equals zero to three, can be used to prepare low valent titanium catalyst for aromatic alkylation and transalkylation of alkylaromatic compounds and particularly those containing methyl and ethyl groups. In order to be candid, it should be known that in U.S. Pat. No. 2,683,759, the use of $TiF_4$ for transalkylation of ethylbenzene in the presence of HF is disclosed. The reaction product of $TiF_4$ with HF is an acid known as $H_2TiF_6$. containing catalysts can be prepared by heating complexes of $TiF_{4-x}Cl_x$ supported on alumina in inert gas flow without the use of reducing agents such as hydrogen or active metals such as sodium, magnesium, aluminum, etc. A novel feature of my new catalyst is the use of titanium tetrafluoride complexes and no use of conventional reducing agents such as hydrogen or active metals to reduce tetravalent titanium ions to specific trivalent ions. When complexes of $TiF_{4-x}Cl_x$ supported on active alumina were heated in a nitrogen gas flow, it was confirmed by ESR spectroscopic technique that tetravalent titanium ions started to reduce at about 300° C. to produce specially coordinated titanium ion species. Titanium tetrafluoride supported on gamma alumina could not be reduced at 300° C. with a hydrogen atmosphere. However, it is known that titanium tetrahalides can be reduced by the use of a hydrogen atmosphere at higher temperatures. By electron spin resonance spectroscopy or ESR spectroscopy, I have found two different titanium trivalent ions species, i.e., ESR active species and ESR inactive species at ambient temperature. Therefore, the two $Ti^{+3}$ ion species containing compounds on the catalyst surface are isomeric but their coordinations are different.

It is well known that many isomers of chemical compounds have different uses, reactivities and physical properties even though they can be expressed by an identical chemical formula. I have found that only ESR active $Ti^{+3}$ species are suitable for the "clean" alkylation reaction of benzene with ethylene to ethylbenzenes and transalkylation of ethylbenzenes. The term "clean" means that there is no preceptable polymerization of ethylene to polyethylene. ESR inactive species are ambitious catalysts for the polymerization of ethylene and practically inactive for the transalkylation of ethylbenzene. When ESR inactive titanium trivalent ion containing catalysts, prepared by hydrogen reduction of tetravalent titanium ions, were tested for the alkylation of benzene with ethylene under pressure to obtain acceptable reaction rates at various temperatures, ethylene molecules were polymerized to high molecular weight polymers. Since the ethylene polymers rapidly plugged the reactor and its associated plumbing, the reactions had to terminate shortly after they were initiated. When the catalysts, prepared by hydrogen reduction, were analyzed with a ESR spectrometer, the catalysts contained no ESR active $Ti^{+3}$ ion species. When the catalysts prepared by hydrogen reduction were tested for the ethylbenzene transalkylation reaction, the catalysts displayed almost no activity. When the catalysts prepared by hydrogen reduction were tested for ethylbenzene transalkylation reaction, the catalysts were essentially inactive. The catalysts prepared by the use of $TiF_4$ complexes and which contained ESR active $Ti^{+3}$ ion species were tested for the transalkylation of ethylbenzene, they were active. The ESR g-valves were 1.937–1.948 at room temperature depending on the temperature and duration of thermal treatment and the type of organic liquid complexes. FIG. 1 is a typical ESR spectrogram of an ESR active $Ti^{+3}$ species on alumina. The spectra was recorded at room temperature after thermal decomposition of 2-methoxy propene complex of $TiF_4$ supported on gamma-alumina at 300° C. for one hour in a flowing helium stream. The g value was 1.939. When a catalyst contained ESR active $Ti^{+3}$ ion species and was exposed to a helium gas flow containing benzene or heptane vapors at room temperature, the peak height of the ESR spectra was reduced. The diminished ESR peak height strongly suggest that the active catalyst sites contain the specific $Ti^{+3}$ ion species.

Figure 2:
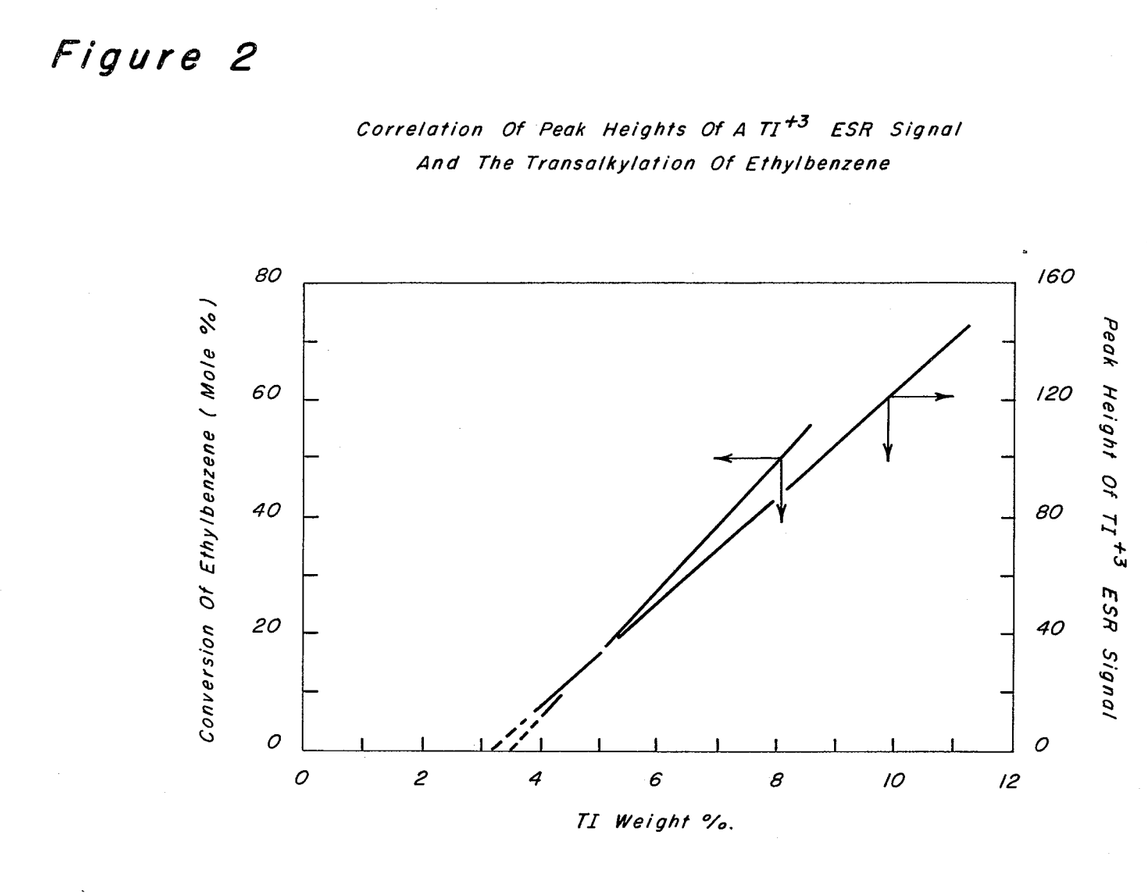

FIG. 2 is a correlation of the relative peak heights of $Ti^{+3}$ ESR signal and the transalkylation of ethylbenzene. The catalyst activities appear to be proportional to the concentration of ESR active $Ti^{+3}$ ion species in the catalysts. Another interesting observation to be made from FIG. 2 is that a critical minimum amount of titanium in the catalyst is required to obtain a suitable catalyst for aromatic conversion reactions. The critical minimum amount of titanium in the catalyst is required to obtain a suitable catalyst for aromatic conversion reactions. The critical minimum amount of titanium on the catalyst may depend on the type of alumina, the concentration of OH groups on the alumina surface, the alumina apparent bulk density (ABD), surface area, thermal treatment temperature, type of $TiF_4$ organic liquid complexes, etc. When 1/16 inch oil dropped, spherical alumina with an apparent bulk density of 0.5, a surface area of about 200 $m^2/g$, a $TiF_4$ complex of methanol and a 500° C. thermal treatment in a nitrogen gas flow was used for the preparation of a catalyst, the critical, minimum amount of titanium in the finished catalyst was approximately 3.25–3.5 weight percent as shown in FIG. 2.

A preferred method of preparation of the catalyst of the present invention is the impregnation of predried active alumina with complexes of $TiF_4$ solutions in organic solvents and then the thermal treatment of the impregnated alumina in an inert gas flow to reduce the tetravalent titanium ions to ESR active trivalent titanium ions. Complexes of $TiF_4$ can be prepared by reacting anhydrous $TiF_4$ with organic compounds selected from the group of compounds containing at least one methoxy group per molecule or compounds having at least one electron donor atom and double bond per molecule. Although methanol and isopropanol are suitable complexing agents, ethanol and the other primary alcohols are not. Mixtures of primary alcohols and organic compounds containing methoxy groups such as methanol, 2-methoxyethanol, 2-methoxypropene, etc. are suitable and alumina impregnated with such mixtures after thermal treatment in an inert atmosphere display ESR active $Ti^{+3}$ ion species. The most effective catalysts can be prepared by first impregnating $TiF_4$ complexes on active alumina rather than supporting anhydrous $TiF_4$ on active alumina and then complexing the supported tetravalent titanium ions with one methoxy group containing organic compounds. Unless the $TiF_4$ is co-impregnated and complexed with the required organic compound, the resulting catalyst will not contain ESR active $Ti^{+3}$ ion species and furthermore will not catalyze the transalkylation of ethylbenzene. However it is possible to prepare catalysts for clean alkylation reactions or transalkylation reactions by supporting $TiF_4$ complexes such as an ethanol complex of $TiF_4$ on active alumina and then exposing the ethanol complex of $TiF_4$/alumina to an organic compound containing a methoxy group before subjecting the intermediate alumina complex to the thermal treatment at elevated temperatures in inert gas flow. Catalyst prepared in this manner will catalyze the clean alkylation of benzene with ethylene and is also active for the transalkylation of ethylbenzene as long as at least the critical amount of titanium is present on the finished catalyst.

If the catalyst is further supported on an inert carrier, any well known inert supports can be used. These include silica, clay, charcoal, gravel, sand etc. though all of these will not give equivalent results.

It is also within the scope of the present invention to add one or more promoters to the catalyst system. It is believed that use of one or more promoters, e.g., Group VIII and Group VI-B metals, may be beneficial to the practice of the present invention.

When it is desired to use the catalyst system in an alkylaromatic isomerization process, then alkylaromatic isomerization reaction conditions should be used. Reaction conditions are disclosed in U.S. Pat. No. 3,637,881 (Class 260–668a), the teachings of which are incorporated by reference. When it is desired to use the catalyst system of the present invention for alkylaromatic transalkylation, then appropriate reaction conditions should also be used. These are disclosed in U.S. Pat. No. 3,720,726 (Class 260–672t), the teachings of which are incorporated by reference. Reaction conditions for the alkylation of aromatic hydrocarbons include a pressure sufficient to maintain a liquid phase in the reaction zone with a preferable pressure range from about 20 to about 60 atmospheres, a temperature in the range from about ambient to about 400° C. with preferred temperatures from about 100° to about 250° C., and a liquid hourly space velocity from about 0.1 to about 20.

It is an object of this invention to present a process for the catalytic conversion of aromatic hydrocarbons and the manufacture of a novel catalyst utilized therein.

In one of the broad aspects, the present invention embodies a novel method of manufacturing a catalyst comprising ESR active $Ti^{+3}$ ion species on a inorganic oxide catalyst.

In one of its broad aspects, the present invention embodies a method of manufacturing a novel catalytic composite which comprises an inorganic oxide and specific titanium compounds which comprises subjecting the inorganic oxide to titanium tetrafluoride complexes of organic compounds selected from the group of compounds containing at least one methoxy group per molecule or compounds having at least one electron donor atom and double bond per molecule.

One of the more specific embodiments of the present invention relates to a method of manufacturing a catalytic composite of alumina and a specific trivalent titanium compound which comprises subjecting the alumina to titanium tetrafluoride complexes of organic compounds selected from the group of compounds containing at least one methoxy group per molecule or compounds having at least one electron donor atom and double bond per molecule and then subjecting the resulting alumina to thermal treatment at elevated temperatures in an inert gas.

Another object of the present invention is to afford a process for the conversion of aromatic hydrocarbons including isomerization, alkylation, transalkylation, etc. Therefore, in one embodiment, the present invention encompasses a process which comprises reacting an aromatic hydrocarbon at conditions which promote the desired reactions.

In another embodiment, the generally broad operating conditions include a pressure of from about 1 to 70 atmospheres, a liquid hourly space velocity of from about 0.1 to about 30, and a maximum catalyst temperature of from about 100° C., to about 400° C.

Other objects and embodiments of my invention relate to additional details regarding preferred catalytic ingredients, the concentration of components in the catalytic composite, methods of catalyst preparation, individual operating conditions for use in the various hydrocarbon conversion processes, preferred processing techniques and the like particulars which are hereinafter described.

A suitable method for the preparation of the catalyst of the present invention is to select suitable sized gamma-alumina particles which have been predried at a temperature in the range of about 250 to about 650° C. in inert gas or hydrogen flow for about 0.1 to about 10 hours. The previously dried alumina is impregnated with solutions of a $TiF_4$ methanol complex in absolute methanol and then subjected to thermal treatment in an inert atmosphere at temperatures in the range of about 50° to about 1000° C.

The catalyst may be disposed in a reactor vessel as a fixed, fluidized or moving bed of catalyst. The reactants may contact the catalyst in upflow, downflow, or crossflow fashion, though upflow of reactants over a fixed bed of catalyst is preferred.

The catalyst and process of the present invention have a number of advantages over the prior art. The use of an alumina support enables the use of a truly fixed bed reaction zone. No additives such as $BF_3$ or other chemicals are required for injection into the reaction zone in order to maintain high catalyst activity. Frequent catalyst regenerations are not needed to obtain active and selective catalyst. Although the catalysts contain low valent titanium ions, they are reasonably stable for brief exposures to air or moisture. The hydrocarbon product doesn't require washing, extraction or catalyst removal. In the case of alkylation of aromatic hydrocarbons, no careful monitoring of the aromatic to olefin ratio is required to prevent undesirable polymerization reactions, and since low benzene to ethylene ratio based on fresh feed can be employed in the alkylation reactor, the benzene recycle can be reduced.

The following examples are presented in illustration of the catalyst of this invention and a method of preparation thereof, and are not intended as an undue limitation on the generally broad scope of the invention as set out in the appended claims.

The alkylation and transalkylation reactions were performed in laboratory scale pilot plant and the catalysts were loaded into ⅜ inch I.D. steel reactors under a nitrogen blanket. Benzene and ethylene were combined prior to introduction into the upflow reactor. The liquid products were collected in a cold trap and analyzed by gas chromatograph (G.C.). The benzene or ethylbenzene was predried by contact with high surface area sodium and the ethylene was predried by contact with 4 A molecular sieves.

EXAMPLE 1—CATALYST A

One hundred cc of spherical 1/16 diameter gamma-alumina was predried at 550° C. for 4 hours with a nitrogen purge stream flowing at the rate of two thousand cc per minute. The resulting dried alumina was impregnated with a solution of titanium tetrafluoride complex of methanol which was prepared by dissolving 8 gms of anhydrous $TiF_4$ in 200 ml of absolute methanol in a $N_2$ atmosphere. The alumina spheres were cold rolled for about ten minutes and then dried in a steam rotary drier under a nitrogen gas flow. The impregnated product was then subjected to a series of thermal treatments with a nitrogen purge stream flowing at the rate of two thousand cc per minute according to the following schedule:

| Temperature, C.° | Period, Hours |
|---|---|
| 140 | 1.0 |
| 200 | 0.5 |
| 250 | 1.25 |
| 300 | 0.25 |
| 450 | 3.0 |

The finished catalyst was cooled and stored under a nitrogen blanket and contained 5.30 weight percent Ti and 7.10 weight percent fluoride. It had a bluish color. This catalyst was tested in Run 47 and catalyzed a clean alkylation reaction. See Table 1 for details.

EXAMPLE 2—CATALYST B

Two hundred and fifty cc of predried gamma-alumina, which was the identical alumina to that used in Example 1, was impregnated with a $TiF_4$ complex solution in a steam rotary drier under a $N_2$ gas flow. The $TiF_4$ complex solution was prepared by dissolving 20 gms of anhydrous $TiF_4$ in about 400 ml of anhydrous $C_2H_5OH$ with a gentle heating in a reflux system under a $N_2$ blanket. About 200 ml of anhydrous $CH_3OH$ was added and then the solution was refluxed for 20 minutes. The aluminum spheres were cold rolled for 30 minutes and then dried. The impregnated product was then subjected to a series of thermal treatments with a nitrogen purge stream flowing at the rate of 2000 cc per minute according to the following schedule:

| Temperature, C.° | Period, Hours |
|---|---|
| 100 | 1.5 |
| 140 | 1.5 |
| 200 | 1.0 |
| 250 | 1.0 |
| 500 | 1.0 |

The finished catalyst was cooled and stored under a $N_2$ blanket and contained 5.90 weight percent Ti and 7.70 weight percent fluoride. It had a blue color. This catalyst was tested in Run 46. This catalyst catalyzed a clean alkylation reaction. See Table 1 for details.

EXAMPLE 3—CATALYST C

Three hundred cc of the identical gamma-alumina used in Example 1 was impregnated with aqueous $H_2TiF_6$ solution prepared by diluting 18.01 grams of 60% aqueous $H_2TiF_6$ solution with 275 ml of de-ionized water. The alumina spheres were cold rolled for 30 minutes and then dried in a rotary steam drier. The impregnated product was dried with a $N_2$ purge stream flowing at the rate of 2000 cc per minute to support tetravalent titanium fluoride on gamma-alumina according to the following schedule:

| Temperature, C.° | Period, Hours |
|---|---|
| 140 | 1.0 |
| 300 | 1.0 |

-continued

| Temperature, C.° | Period, Hours |
|---|---|
| 500 | 1.0 |

The white, dried product was loaded into a steam rotary drier under a N₂ blanket and 300 ml of absolute methanol were added. The spheres were cold rolled for 10 minutes and then dried under a N₂ gas flow. The dried product was subjected to the thermal treatment according to the following schedule:

-continued

| Temperature, C.° | Period, Hours | Gas Flow Rate |
|---|---|---|
| 550 | 3.0 | 1000 cc/min H₂ |

The finished catalyst was cooled and stored under a N₂ blanket and contained 7.27 weight percent Ti and 7.13 weight percent fluoride. This catalyst was tested in Run 76. This catalyst polymerized ethylene. See Table 1 for details.

TABLE 1

| Catalyst | A | B | C | D | E | F | F | G | G | G |
|---|---|---|---|---|---|---|---|---|---|---|
| | | | | ALKYLATION | | | | | | |
| Ti Wt. % in Catalyst | 5.30 | 5.90 | 5.27 | 7.27 | 2.04 | 7.80 | 7.80 | 7.90 | 7.90 | 7.90 |
| Run | 47 | 46 | 50 | 76 | 51 | 95 | 95 | 85 | 85 | 85 |
| Volume of Catalyst (cc) | 25 | 50 | 25 | 50 | 50 | 100 | 100 | 100 | 100 | 100 |
| Hours On Stream | 24–28 | 32–36 | — | — | — | 174–186 | 211–216 | 100–106 | 322–328 | 826–832 |
| Reaction Condition | | | | | | | | | | |
| Reactor Temp. °C. | 181 | 197 | 200 | 230 | 200 | 179 | 180 | 230 | 228 | 229 |
| Reactor Press., psig | 492 | 500 | 500 | 500 | 500 | 208 | 352 | 500 | 498 | 510 |
| LHSV based on fresh benzene feed | 10.1 | 6.0 | 6.0 | 5.97 | 6.0 | 2.07 | 2.02 | 1.0 | 0.98 | 0.96 |
| Recycle Rate (LHSV) | None | None | None | None | None | 7.81 | 6.35 | 1.97 | 1.95 | 2.14 |
| C₆H₆/C₂H₆ Mole Ratio | 2.6 | 2.5 | 4.0 | 3.92 | 4 | 1.82 | 2.23 | 4.3 | 2.0 | 1.1 |
| Ethylene Conversion (%) | 70.0 | 93.5 | — | — | — | 99+ | 100 | 100 | 100 | 100 |
| Composition of Alkylation Reactor Effluent (wt. %) | | | | | | | | | | |
| Nonaromatics | 0.5 | 0.3 | Ethylene Polymerization | Ethylene Polymerization | Ethylene Polymerization | 0.26 | 0.17 | 0.10 | 0.13 | 0.17 |
| Benzene | 79.6 | 65.3 | | | | 56.16 | 59.71 | 73.05 | 51.83 | 34.64 |
| Ethylbenzene | 13.1 | 23.9 | | | | 22.20 | 22.24 | 23.88 | 34.67 | 27.17 |
| Diethyl benzene | 3.8 | 7.7 | | | | 9.85 | 9.31 | 2.66 | 11.34 | 22.59 |
| Butyl benzene | 0.1 | tr | | | | 0.32 | 0.28 | 0.03 | 0.09 | 0.25 |
| Triethyl benzene | 1.1 | 1.8 | | | | 4.44 | 3.80 | 0.11 | 1.47 | 10.75 |
| Tetraethyl benzene | 0.7 | 0.7 | | | | 2.74 | 2.31 | — | 0.17 | 3.65 |
| Pentaethyl benzene | 1.0 | 0.3 | | | | 2.62 | 1.36 | — | — | 0.28 |
| Hexaethyl benzene | 1.0 | 0.3 | | | | 0.50 | 0.16 | — | — | — |
| Diphenyl ethane | 1.0 | 0.3 | | | | 0.45 | 0.33 | 0.12 | 0.17 | 0.27 |
| Heavies | 1.0 | 0.3 | | | | 0.45 | 0.37 | 0.05 | 0.13 | 0.22 |

| Temperature, C.° | Period, Hours |
|---|---|
| 100 | 1.0 |
| 140 | 1.0 |
| 200 | 1.5 |
| 250 | 1.0 |
| 500 | 1.0 |

The finished catalyst was cooled and stored under a nitrogen blanket and contained 5.27 weight percent Ti and 7.6 weight percent fluoride. It had a blue color. This catalyst was tested in Run 50. This catalyst polymerized ethylene. See Table 1 for details.

EXAMPLE 4—CATALYST D

Two hundred cc of predried gamma-alumina, which was the identical alumina used in Example 1, was impregnated with aqueous H₂TiF₆ solution in a steam rotary drier. The H₂TiF₆ solution was prepared by diluting 48.2 grams of 60% aqueous H₂TiF₆ solution with 150 ml of de-ionized water. The alumina spheres were cold rolled for 30 minutes and then dried. The impregnated product was subjected to further drying and hydrogen reduction in N₂ and H₂ flow according to the following schedule:

| Temperature, C.° | Period, Hours | Gas Flow Rate |
|---|---|---|
| 140 | 1.5 | 1500 cc/min N₂ |
| 300 | 1.0 | 1500 cc/min N₂ |

EXAMPLE 5—CATALYST E

Two hundred and fifty cc of predried gamma-alumina, which was the identical alumina used in Example 1, was impregnated with a TiF₄ complex solution in a rotary steam drier under a N₂ gas flow. The TiF₄ complex solution was prepared by dissolving 7 grams of anhydrous TiF₄ in 500 ml of absolute methanol under a nitrogen blanket. The spheres were cold rolled for 10 minutes and then dried. The impregnated product was subjected to a series of thermal treatments with a N₂ purge stream flowing at the rate of 2000 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

The finished catalyst was cooled, stored in a N₂ blanket and contained 2.04 weight percent Ti and 3.0 weight percent fluoride. It had a blue color. This catalyst was tested in Run 51 for alkylation. It polymerized ethylene as expected from FIG. 2.

EXAMPLE 6—CATALYST F

Two hundred cc of predried gamma-alumina, which is the identical alumina used in Example 1, was impregnated with a solution of TiF₄ complex of 2-methoxyethanol in a steam rotary drier under a N₂ gas flow. The complex solution was prepared by dissolving 24 grams of anhydrous $TiF_4$ in 400 ml of 2-methoxyethanol and the solution was refluxed for about 30 minutes under a $N_2$ gas flow. The alumina spheres were cold rolled for 30 minutes and then dried. The impregnated product was subjected to a series of thermal treatments with a $N_2$ purge stream flowing at the rate of 1500 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

The finished catalyst was cooled, stored under a $N_2$ blanket and contained 7.80 weight percent Ti and 9.77 weight percent fluoride. It had a blue color. The catalyst was tested in Run 95. It catalyzed a clean alkylation reaction. See Table 1 for details.

EXAMPLE 7—CATALYST G

Three hundred and twenty-five cc of predried gamma-alumina, which was the identical alumina used in Example 1, was impregnated with a solution of $TiF_4$ complex which was prepared by dissolving 39.0 grams of anhydrous $TiF_4$ in 350 ml of absolute methanol and refluxing for 30 minutes under a $N_2$ gas flow. The alumina spheres were cold rolled for one hour and then dried. The impregnated product was subjected to a series of thermal treatments with a nitrogen purge stream flowing at the rate of 1500 cc per minute according to the following schedule:

| Temperature, C.° | Period, Hours |
|---|---|
| 140 | 1.5 |
| 200 | 1.0 |
| 250 | 1.0 |
| 500 | 1.0 |

The finished catalyst contained 7.9 weight percent Ti and 8.9 weight percent fluoride. It had a blue color and was tested in Run 85. The alkylation reaction was clean. See Table 1 for details.

EXAMPLE 8

Two hundred and fifty cc of predried gamma-alumina, which was the identical alumina in Example 1, was impregnated with a solution of $TiF_4$ complex of methanol in a steam rotary drier under a $N_2$ gas flow. The solution of $TiF_4$ complex was prepared by dissolving 20 grams of anhydrous $TiF_4$ in 400 ml of absolute methanol and then refluxing for about 30 minutes under a $N_2$ blanket. The alumina spheres were cold rolled for 10 minutes and then steam dried. The impregnated product was subjected to a series of thermal treatments with a $N_2$ purge stream flowing at the rate of 1500 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

The finished catalyst was cooled in a nitrogen blanket and had a blue color. This catalyst was subjected to the second impregnation with a solution of $TiF_4$ complex of methanol in a similar manner as above. The solution was prepared by reacting 10 grams of anhydrous $TiF_4$ with 500 ml of absolute methanol. The catalyst spheres were cold rolled for 10 minutes and then dried. The impregnation product was again subjected to the identical thermal treatments as before. The finished catalyst was cooled and stored in a nitrogen blanket. This catalyst had 7.83 weight percent Ti and 10.07 weight percent fluoride. The catalyst was blue in color. When 10 cc (5.63 gms) of this catalyst was loaded into the reactor, the catalyst was accidentally loaded in air. Since the catalyst was exposed to air, the initial conversion of ethylene was less than 18 percent. The reaction condition was 20 LHSV based on fresh benzene feed, 500 psig, 229° C. and 4 benzene to ethylene mole ratio with no recycle of reaction effluent. When the reaction was continued, the conversion was increased to 59 percent after about 100 hours on stream, showing about 74 percent activity recovery compared with the activity of unpoisoned catalyst. This result showed that although my novel catalyst contained a low valent titanium compound, it was remarkably stable. Considering that the catalyst was subjected to the second impregnation, it was learned that methanol did not destroy the active sites of the finished catalyst and electron donor atom containing molecules such as methanol molecules could be desorbed by heating poisoned catalyst in an inert gas flow without detectable destruction of active sites.

Since the active sites of the catalyst appeared to consist of ESR active $Ti^{+3}$ ion species, the catalyst stability was studied by using ESR spectrometer. Three hundred and sixty cc of predried gamma-alumina which was the identical alumina used in Example 1, was impregnated with a solution of $TiF_4$ complex of methanol in a steam rotary drier under a nitrogen gas flow. The complex solution was prepared by dissolving 57.6 gms of anhydrous $TiF_4$ in 400 ml of absolute methanol and refluxing the solution for 30 minutes in a nitrogen gas flow. The aluminum spheres were cold rolled for 1 hour and then dried. After thermal treatment, the finished catalyst contained 10.7 percent Ti and 9.2 percent fluoride. When a small amount of impregnated product before thermal treatment was heated at 500° C. for 1 hour in a He gas flow and then the concentration of ESR active $Ti^{+3}$ ion species was measured in terms of peak height of ESR spectra recorded at room temperature, the peak height was 62 on arbitrary scale and the g value was 1.945. When this catalyst was exposed to air flow for 15 minutes at room temperature and then the peak height was measured again, the peak height was 40. This air exposed catalyst was heated consecutively at a series of temperatures, 200°, 300° and 500° C. for each 1 hour in He gas flow and then ESR spectrum were recorded after each heating. There was almost no change of peak height after heating at 200° and 300° C. However, after heating at 500° C., the peak height increased to 58. Another small portion of the impregnated product was subjected to the thermal treatment at 500° C. in He gas flow. The peak height of ESR spectrum was 56 on the same arbitrary scale. When this catalyst was exposed to water vapor saturated He gas flow for 15 minutes at room temperature, the peak height was reduced to 38. While heating this water poisoned catalyst consecutively at 200°, 300° and 500° C. for each 1 hour in He gas flow the ESR spectrum were recorded after each treating step. There was again little change of peak height after heating at 200° and 300° C. But after heating at 500° C. the peak height of ESR spectra grew to 60. The above two experiments demonstrated that oxygen or water will inhibit catalytic reaction, and that the adsorbed poisons could be removed by heating at high temperatures in inert gas flow.

EXAMPLE 9—CATALYST H

This example illustrates the preparation of a catalyst and the transalkylation of ethylbenzene according to the method of the present invention. A 250 ml batch of spherical 1/16 inch diameter gamma-alumina was predried at 550° C. for three hours with a nitrogen purge stream flowing at the rate of 2000 cc per minute. The resulting dried alumina was impregnated with a solution $TiF_4$ complex which was prepared by dissolving 20 gms. of anhydrous titanium tetrafluoride in about 500 ml of absolute methanol in a nitrogen atmosphere. The alumina spheres were cold rolled for about 10 minutes and then dried in a steam rotary dried under a nitrogen atmosphere. The impregnated product was then subjected to a series of thermal treatments with a nitrogen purge stream flowing at the rate of 2000 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

The finished catalyst was cooled and stored under a nitrogen blanket and contained 5.53 weight percent titanium and 7.7 weight percent fluoride. The finished catalyst had a blue color and was tested in Run 604 for the transalkylation of benzene. This catalyst was active. See Table 2 for further details.

EXAMPLE 10—CATALYST I

A 250 ml batch of 1/16 inch spherical diameter gamma-alumina was predried at 550° C. for three hours with a nitrogen purge stream flowing at the rate of 2000 cc per minute. The resulting dried alumina was mixed with 20 gms of anhydrous titanium tetrafluoride powder in a nitrogen atmosphere. This mixture was loaded in vertical tube and then heated at 300° C. for two hours and 450° C. for 1.5 hours with a nitrogen purge stream flowing at the rate of 200 cc per minute. The product of the hereinabove described procedure was placed into 300 ml. of absolute methanol, cold rolled for ten minutes and then dried in a steam rotary dried under a nitrogen atmosphere. The resulting alumina particles were then subjected to a series of thermal treatments with a nitrogen purge stream flowing at the rate of 2000 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

TABLE 2
TRANSALKYLATION OF ETHYLBENZENE

| Catalyst | H | E | I | I | J |
|---|---|---|---|---|---|
| Ti Wt. % in the Catalyst | 5.53 | 2.04 | 5.14 | 6.14 | 11.7 |
| Run | 604 | 608 | 613 | 613 | 611 |
| Volume of Catalyst | 50 | 50 | 50 | 50 | 50 |
| Hours On Stream | 140–144 | 17–21 | 9–13 | 29–33 | 25–29 |
| Reaction Condition | | | | | |
| Reactor Temp., °C. | 200 | 200 | 200 | 220 | 180 |
| Reactor Press., psig | 500 | 500 | 500 | 500 | 500 |
| LHSV | 4 | 4 | 4 | 4 | 4 |
| Composition of Reactor Effluent (wt. %) | | | | | |
| Nonaromatics | — | 0.1 | — | — | — |
| Benzene | 9.8 | tr | 0.2 | 1.8 | 15.0 |
| Ethylbenzene | 74.6 | 99.9 | 99.5 | 95.1 | 61.0 |
| Diethylbenzene | 15.0 | — | 0.3 | 3.1 | 22.6 |
| Butylbenzene | tr | — | — | — | — |
| Triethylbenzene | 0.5 | — | — | — | 1.4 |
| Heavies | — | — | — | — | — |

The finished catalyst was cooled and stored under a nitrogen blanket and contained 5.14 weight percent titanium and 7.7 weight percent fluoride. The catalyst had a blue color and was tested in Run 613 for the transalkylation of ethylbenzene. This catalyst was practically inactive. See Table 2 for further details.

EXAMPLE 11—Catalyst J

Two hundred and fifty cc of predried gamma-alumina, which was the identical alumina used in Example 1, was impregnated with a solution of $TiF_4$ complex of methanol in a steam rotary drier under a $N_2$ gas flow. The complex solution was prepared by dissolving 20 gms. of anhydrous $TiF_4$ in 450 ml of absolute methanol in a $N_2$ atmosphere. The alumina spheres were cold rolled for 10 minutes and then dried. The impregnated product was again impregnated with 450 ml solution of $TiF_4$ complex of methanol which was prepared in the same manner as above. The impregnated product was subjected to a series of thermal treatments with a nitrogen purge stream flowing at a rate of 200 cc per minute according to the following schedule:

| Temperature, C.° | Period, Hours |
|---|---|
| 100 | 1.0 |
| 140 | 1.5 |
| 200 | 1.0 |
| 250 | 1.0 |
| 500 | 1.0 |

The finished catalyst was cooled and stored in a nitrogen blanket. This catalyst contained 11.7 weight percent Ti and 11.9 weight percent fluoride. The catalyst had blue color and was tested in Run 611 for the transalkylation of ethylbenzene. This catalyst was active. See Table 2 for details.

EXAMPLE 12—Catalyst E

The catalyst E in Example 5, which contained 2.04 weight percent Ti and 3.0 weight percent fluorine was tested for transalkylation of ethylbenzene in Run 608. It was inactive as expected from FIG. 2. This example and Example 5 demonstrate that if a catalyst was not active for transalkylation of ethylbenzene, the catalyst will polymerize ethylbenzene or vice versa. See Table 2 for details.

EXAMPLE 13—Catalyst K

Two hundred cc of predried gamma-alumina, which was the identical alumina used in Example 1, was impregnated with a solution TiF$_4$ complexes of ethanol in a steam rotary drier under a N$_2$ gas flow. The complex solution was prepared by dissolving approximately 5 gms of anhydrous TiF$_4$ in 500 ml of absolute ethanol and refluxing the solution for about 10 minutes under a N$_2$ blanket. The alumina spheres were cold rolled for 10 minutes and then dried. Then impregnated product was subjected to a series of thermal treatments with a N$_2$ purge stream flowing at a rate of 1500 cc per minute according to the following schedule:

| Temperature, C.° | Period, Hours |
|---|---|
| 140 | 1.0 |
| 200 | 1.5 |
| 250 | 1.0 |
| 300 | 0.25 |
| 450 | 3.0 |

The finished catalyst contained 1.76 weight percent Ti and 2.8 weight percent fluoride. This catalyst had a white color. Since the Ti$^{+4}$ ions were not reduced, it was not even tested.

EXAMPLE 14—Catalyst L

Three hundred and twenty-five cc of predried gamma-alumina, which was the identical alumina used in Example 1, was impregnated with a solution of TiF$_4$ complex of methanol in a steam rotary drier under N$_2$ flow. The slution was prepared by dissolving 39.0 grams of anhydrous TiF$_4$ in 350 ml of absolute methanol and refluxing for 30 minutes in a N$_2$ blanket. The alumina spheres were cold rolled for one hour and then dried. The impregnated product was subjected to a series of thermal treatments with a nitrogen purge stream flowing at a rate of 1500 cc per minute according to the following schedule:

| Temperature, C.° | Period, Hours |
|---|---|
| 140 | 1.5 |
| 200 | 1.0 |
| 250 | 1.0 |
| 500 | 1.0 |

The finished catalyst was cooled and stored in a nitrogen blanket. It had a blue color and contained 7.90 percent Ti and 8.7 percent fluoride.

Fifty cc (28.5 gms) of catalyst was loaded in a glass tube and glass wool was packed on the top of the catalyst. Pure m-xylene was charged to the top of the glass wool at the desired reaction temperatures and ambient pressure to vaporize the m-xylene. The m-xylene vapor was mixed with N$_2$ carrier gas and the gas mixture was passed downward over the catalyst. The reaction products were collected in an ice trap. The pure m-xylene was used without drying or purification. The results are listed in Table 3. The results showed that this catalyst catalyzed the isomerization of m-xylene to p- and o-xylene. There was also substantial transalkylation reaction products. Therefore, it is shown that this catalyst can catalyze the isomerization and transalkylation of alkylaromatic compounds.

The foregoing specification and examples illustrate the improvements encompassed by the present invention and the benefits to be afforded therefrom.

TABLE 3

| | ISOMERIZATION | | | | |
|---|---|---|---|---|---|
| Catalyst | L | L | L | L | L |
| Rection Temp., °C. | 270 | 250 | 320 | 350 | — |
| WHSV of m-xylene | 0.51 | 0.45 | 0.40 | 1.16 | — |
| N$_2$ (cc/min) | 100 | 100 | 100 | 100 | — |
| | — | — | — | — | Feed |
| Composition of Reaction Product (wt.%) | | | | | |
| Nonaromatics | 0.03 | — | 0.01 | tr | — |
| Benzene | 0.02 | tr | 0.04 | 0.05 | — |
| Toluene | 7.05 | 1.53 | 8.61 | 8.62 | 0.07 |
| Ethylbenzene | — | — | — | — | 0.17 |
| P-Xylene | 17.66 | 11.97 | 19.11 | 19.48 | — |
| O-Xylene | 17.27 | 13.55 | 17.61 | 17.08 | 0. |
| M-Xylene | 48.61 | 71.02 | 42.77 | 43.82 | 99. |
| 1,3,5 TMBz | 2.66 | 0.57 | 3.19 | 3.00 | — |
| 1,2,4 TMBz | 5.74 | 1.21 | 7.21 | 7.00 | — |
| 1,2,3 TMBz | 0.65 | 0.13 | 0.90 | 0.92 | — |
| 1,2,4,5 TeMBz | 0.14 | — | 0.23 | — | — |
| 1,2,3,5 TeMBz | 0.17 | — | 0.27 | — | — |
| 1,2,3,4 TeMBz | tr | — | 0.05 | — | — |

I claim as my invention:

1. A process for the catalytic conversion of an aromatic hydrocarbon comprising contacting the aromatic hydrocarbon with a reactant in the presence of a catalyst which contains ESR active Ti$^{+3}$ species and is prepared by subjecting alumina to anhydrous tetravalent titanium fluoride complexes of an organic compound selected from the group of organic compounds containing at least one methoxy group per molecule or organic compounds having at least one electron donor atom and double bond per molecule, and heat treating the resulting impregnated alumina in an inert atmosphere, and recovering a converted aromatic hydrocarbon as a product of the process.

2. The process of claim 1 wherein said organic compound is methanol.

3. The process of claim 1 wherein said organic compound is 2-methoxyethanol.

4. The process of claim 1 wherein said organic compound is 2-methoxypropene.

5. The process of claim 1 wherein said heat treating is performed at a temperature between about 50° C. and about 1000° C.

6. The process of claim 1 wherein said inert atmosphere comprises nitrogen.

7. The process of claim 1 wherein said heat treating is performed at 250° C. to 650° C. for 10 hours.

8. The process of claim 1 wherein the alumina has an apparent bulk density of about 0.3 to about 0.8 g/cc and a surface area of about 1 to about 500 m$^2$/g.

9. The process of claim 1 wherein said catalyst contains, on an elemental basis, about 0.5 to about 20 weight percent titanium.

10. The process of claim 1 wherein the aromatic hydrocarbon is selected from the group consisting of bezene, toluene, ethylbenzene, xylene and propyl benzenes.

11. The process of claim 1 wherein the reactant is selected from the group consisting of an olefin and aromatic hydrocarbons.

12. The process of claim 1 wherein the conversion reaction which occurs is alkylation of an aromatic compound with an alkylating agent.

13. The process of claim 12 wherein benzene is alkylated with an olefin selected from the group of ethylene and propylene.

14. The process of claim 12 wherein benzene is alkylated with an olefin selected from the group of $C_4$ to $C_{18}$ olefins.

15. The process of claim 1 wherein said tetravelent titanium fluoride is $TiF_4$.

16. The process of claim 1 wherein said tetravalent titanium fluoride is $TiF_3Cl$.

* * * * *